United States Patent [19]

Pimenov et al.

[11] Patent Number: 5,705,269
[45] Date of Patent: Jan. 6, 1998

[54] MODIFIED ACTIVATED CARBON

[75] Inventors: Alexander V. Pimenov; Alexander L. Lieberman, both of St. Petersburg, Russian Federation; Joseph L. Shmidt, Brooklyn, N.Y.

[73] Assignee: Electrophor, Inc., Dobbs Ferry, N.Y.

[21] Appl. No.: 665,579

[22] Filed: Jun. 18, 1996

Related U.S. Application Data

[63] Continuation of Ser. No. 378,644, Jan. 26, 1995, abandoned.

[30] Foreign Application Priority Data

Feb. 1, 1994 [RU] Russian Federation ................. MKI(5)COIB3108
Jul. 4, 1994 [RU] Russian Federation .. N94-0249-5126(

[51] Int. Cl.⁶ .................... B01D 39/04; B01D 39/16
[52] U.S. Cl. .................... 428/375; 428/401; 428/408
[58] Field of Search .................... 428/375, 401, 428/408

[56] References Cited

U.S. PATENT DOCUMENTS

| | | | |
|---|---|---|---|
| 3,325,402 | 6/1967 | Mortimer | 210/64 |
| 4,238,334 | 12/1980 | Halbfoster | 210/679 |
| 4,789,475 | 12/1988 | Harte et al. | 210/502.1 |
| 4,929,502 | 5/1990 | Giglia | 428/357 |
| 4,966,872 | 10/1990 | Horowitz et al. | 502/7 |
| 5,032,281 | 7/1991 | Nagamotsu et al. | 210/651 |
| 5,360,734 | 11/1994 | Chapman et al. | 435/238 |

*Primary Examiner*—Kathleen Choi
*Attorney, Agent, or Firm*—Robert I. Pearlman

[57] ABSTRACT

An activated carbon is modified to have bactericidal properties and/or an additional ability to remove heavy metals and other toxic substances. Said modified activated carbon is especially suitable for purifying drinking water and can be readily modified to be suitable for various regions with specific tap water impurities. Pursuant to the invention, activated carbon fiber is treated to adsorb a member of the group consisting of cations, anions, organic complex forming agents, surfactants, polyelectrolytes and organic bactericidal compounds.

3 Claims, No Drawings

MODIFIED ACTIVATED CARBON

This is a continuing application of U.S. Ser. No. 08/378,644 filed Jan. 26, 1995, now abandoned.

BACKGROUND OF THE INVENTION

Municipally treated or untreated tap water has at least some of the following impurities: suspended solids, bacteria, organic matter, heavy metals, metals imparting hardness, anions, chlorine and dissolved gases. The make up and concentration of impurities typically varies from region to region. Bacteria, hazardous organic substances, heavy metal ions and chlorine are especially harmful and should preferably be removed from tap water. This invention relates to the production of the modified activated carbon fiber materials, which are used as adsorbents for extracting such unwanted components from fluids. The term "ACF" in the present specification denotes activated carbon fiber. Said modified ACF has adsorbing capacity similar to common ACF but additionally comprises bactericidal and/or ion-exchange or complex forming agents physically attached onto its surface. It is especially effective for drinking water purification.

Activated carbon fibers (referred to as ACF) or other forms of carbon such as powders are manufactured by activating carbonized material at an elevated temperature in an activating gas atmosphere, typically steam and/or carbon dioxide and/or ammonia. Carbonized fibers are made by carbonizing polyacrylonitrile, phenol resin, pitch or cellulose fibers in an inert atmosphere. In conventional carbonization, the organic material is heated to 200° to 800° C., typically over 400° C. for sufficient time to remove low molecular weight organics and tars leaving more than 90% carbon, typically in the form of crystalline-amorphous structures (graphite layers) rather than a porous structure. Use of steam or $CO_2$ is avoided to retain the carbon fiber strength. Pretreatment steps prior to carbonization are known in the art. After carbonization the carbonized material is activated at temperatures between 800° C. to 1200° C. in an active atmosphere comprising steam and/or carbon dioxide.

Activated carbons and, especially, known activated carbon fibers, have good adsorption capacity toward organic substances and an excellent ability to remove chlorine from water. Additionally, activated carbon fiber may have a small ion-exchange capacity. It is known in the prior art that bacteriostatic or bactericidal properties may be added to the adsorbent by attaching either silver or iodine. However, both silver and iodine, especially iodine, have the disadvantage of exhibiting harmful side effects. Iodine is especially dangerous due to its effect on the thyroid.

A number of the activated carbon modification methods has been proposed in the prior art. U.S. Pat. No. 4,831,011 to Oikawa et al. describes activated carbon with electron-donative surface functional groups which are bonded directly and chemically to graphite constructing the surface of the active carbon. The functional groups are coordinated with metallic ions to form chelate structures. This material is claimed to have an adsorbing power similar to that of common activated carbon as well as the ability to remove specific harmful gas molecules, i.e. ozone, as well as odorous gas molecules from air. Said carbon-based adsorbent is formed by a process comprising exposure of the active carbon to ozone or immersion of the active carbon in an aqueous concentrated hydrogen peroxide solution or a solution of sulfuric acid, which leads to covalent attachment of hydroxyl (—OH), carboxyl (—COOH), formyl (—CHO) and carbonyl (>C=O) groups, and then immersing the treated active carbon in a solution containing metallic ions.

U.S. Pat. No. 4,366,085 to Ikegani describes a fibrous activated carbon with a metal chelate compound supported thereon which is suitable for removal of toxic substances in gas. This activated carbon is produced by first attaching a solution of a chelating agent into the fibrous activated carbon, and then attaching a solution of a heavy metal (Groups Ib, IIa, IIb, VIa, VIIa and VIII) onto the fibrous activated carbon, which is then dried. The heavy metal modified activated carbon is claimed to provide efficient removal of ozone from air. In contrast to the heavy metal chelates of the reference, the present invention uses sodium or other light metals (potassium or hydrogen ions) which are not as firmly bound to the organic chelate structure as heavy metals. The present modified ACF removes heavy metals from water as the sodium diffuses into solution while the heavy metal is adsorbed.

Both of these prior art methods (concentrated acid washing for covalent attachment of weak acidic groups onto the ACF followed by Fe(II) attachment, and adsorbing chelate complexes with metal ions onto the ACF surface) are limited in their ability to produce only metal chelate complexes on the activated carbon surface for securing ozone reduction. Furthermore, covalent bonding to carbon as proposed in the first method involves use of strong acids, making it expensive and requiring extensive washing steps.

U.S. Pat. No. 4,576,929 to Shimazaki et al. describes fibrous activated carbon derived from acrylic fibers by preoxidizing, activating and acid treating. Said fibrous activated carbon is treated with an aqueous solution of silver sulfate. Silver is adsorbed thereby producing silver-containing ACF. Said silver-containing ACF has been shown to have bactericidal properties. Activated carbon with silver supported thereon however has the disadvantages that silver is expensive, it exhibits mostly only bacteriostatic effects, and its concentration in tap water should not exceed 50 parts per billion according to EPA regulations. The present invention distinguishes over this reference since it uses bactericidal organic compounds which do not contain silver. Silver is expensive and leaches into water.

Accordingly the prior art methods and products have the disadvantage of not providing efficient and inexpensive means for producing a modified ACF material with bactericidal and/or ion-exchange or complex forming properties which can be suitably modified for different water purification problems. In addition to organic matter, bacteria and/or heavy metal cations and or anions, other harmful substances may have to be removed from a particular water source. The present invention provides the means to secure this result.

SUMMARY OF THE INVENTION

The invention comprises an improved activated carbon fiber material (derived from ACF by carbonizing and activating cellulose fiber) or non-fibrous material similarly derived which in addition to its ability to adsorb organic matter, is modified to have additional bactericidal and/or ion-exchange and/or other adsorption properties. The invention also relates to the process for producing such a modified adsorbent and for regenerating such adsorbent. The present adsorbent comprises an activated carbon fiber matrix with organic compounds physically adsorbed onto its surface. Said organic compounds form strong physical bonds to the activated carbon matrix and have functionally active groups in their structure providing, for example, bactericidal, cation-exchange, anion-exchange, heavy metal complex formation or other additional desired properties.

While the preparation of a modified activated carbon fiber product is preferred, the product of the present invention may be in other forms, such as powders or granules either by subdividing a carbon fiber product or directly modifying carbonized powders or granules which have been activated at 800°–1200° C. in the presence of steam and/or carbon dioxide.

This adsorbent is especially useful for removing harmful substances from tap water. To be suitable for tap water purification, the modified adsorbent should have a number of different properties simultaneously, such as a large organic adsorption capacity, bactericidal adsorption ability for a wide range of bacteria and viruses, and preferential heavy metal ion-exchange capacity.

In addition to tap water purification, the present process of producing a modified adsorbent can be used to make specialized modified adsorbents for high value added applications in chemistry, biochemistry and medicine. In many instances separation problems in chemistry and in medicine are hindered by the absence of a suitable adsorbent for each particular problem faced. The adsorbent must be selective toward a specific type of impurity.

When two or more impurities having different physical or chemical properties must be removed for a fluid two or more modifying agents are adsorbed simultaneously or consecutively onto the carbon matrix.

In the present invention coupling of functional groups to the surface of the chemically inert matrix is done by adsorption instead of traditional chemical reactions. This allows an adsorbent to be produced with required characteristics by a much easier process. An activated carbon fiber material with required adsorption properties toward a given additive is produced by choosing a suitable modification additive among the numerous suitable organic compounds taught.

When using carbon fiber as the activated carbon, the diameter of the carbon fiber used as precursor material may typically vary from 1 to 30 microns, preferably 2 to 10 microns. The ultimate product may be a non-woven cloth, fabric and alternative forms.

The following examples will serve to illustrate the present invention. Unless otherwise indicated, all part and percentages in the specification are by weight.

The carbonized fiber which was used in the Examples below was purchased from Kuibishev Fiber Corporate (White Russian Republic). It was made by immersing rayon fiber into a solution of silicon-carbohydrate surfactant in carbon tetrachloride, removing the excess solution, and carbonizing the treated rayon fiber at 150° to 350° C. and then at 400° to 800° C. for a total of 72 hours.

DETAILED DESCRIPTION OF THE INVENTION

The activated carbon fiber used in the examples below was produced by activating pretreated carbonized cellulose fiber at 950° to 1100° C.

In the present modification process the organic compounds denoted below are adsorbed on the carbon matrix. Said organic compounds comprise a member of the group consisting of: organic cations and/or anions, organic complex formers (i.e., chelates), ionic and/or non-ionic surfactants, polyelectrolytes or other compounds, which can be adsorbed onto the surface of the activated carbon matrix, so as to provide active functional groups which can adsorb solutes or additives which should be removed from liquid media.

In order to adsorb cations from solutions, at least one of the following types of organic compounds, which are adsorbed onto the carbon matrix, can be used as modifying additives: organic anions, such as alkyl or aryl sulphonates; organic complex forming compounds, such as ethylene diaminetetraacetate (EDTA), diethylenetriaminepentaacerate and trans-1,2diaminocyclohexanetetraacetate; organic anionic surfactants, such as dodecylsulphate; organic polyelectrolytes, such as polyethyleneamone, and polyacrylic acid.

In order to adsorb anions from solution, at least one of the following types of organic compounds can be used as modifying additives: organic cations, such as, four-valent ammonia or aromatic cations comprising hetero-atoms; organic cationic surfactants, such as, cetylpyridinium chloride; and organic polyelectrolytes, such as, polyethyleneamine.

Bactericidal ability can be added to the activated carbon fiber by adsorbing onto the activated carbon a suitable organic bactericide which contains in its structure active bactericidal groups, i.e., groups containing secondary, tertiary or quarterly nitrogen, and also structures which are capable of being adsorbed onto the surface of the activated carbon fiber, i.e., aromatic structures, as for example, brilliant green or rivanol (6,9-diamino-2-ethoxyacridine lactate) and organic halogenates (Cl or Br). These bactericides are cationic. Other suitable organic bactericides include benzyl alcohol, succinchlorimide, nitractin, zephiran, para amino phenol, sodium pentachlorphenolate and N-alkyl-2-methyl-5-ethyl-piridinium.

The adsorption step is normally conducted at 0° to 90° C., preferably 10° to 40° C., for 5 seconds to 2 hours. Reaction times of 15 seconds to 10 minutes are preferred. The concentration of the modifying agent in the treating solution can vary from 1 microgram/gram of fiber, to its maximum solubility depending the adsorbing agent.

Ion-exchange capacity of the activated carbon fiber before and after the activation were determined in the present specification by using static exchange capacity (SEC) tests for both acidic and basic groups. Cation-exchange capacity of ACF was determined by taking a 250 ml flask containing 100 ml of 0.1M NaOH in 1M NaCl solution and 1 gram of ACF and shaking it for 24 hours. The solution was then filtered through filter paper and titrated with 0.1M HCl to determine the amount of base neutralized by acidic groups of ACF. Anion-exchange capacity of ACF was determined in the same manner by using hydrochloric acid instead of sodium hydroxide solution.

EXAMPLE 1

One gram of the activated carbon fiber adsorbent was placed into an adsorption column. 50 ml of 0.01M sodium benzenesulphonate solution was then passed through the column at 20 ml/min. After that 200 ml of 1N hydrochloric acid solution was passed through the column at a rate of 20 ml/min and a temperature of 25° C. to transfer the ion-exchange groups into the H-form. Sodium ions which were adsorbed onto the fibers were replaced with hydrogen ions. Thus the material obtained had acidic properties. Then the column was washed with a large quantity of distilled water (10 liters) to remove weakly bound additive molecules and traces of acid.

To determine the adsorption properties of the modified material, the modified carbon fibers were removed from the column, dried with air and tested for static exchange capacity (SEC). The SEC of the modified carbon fiber was 0.95 meq/gm. The initial untreated activated carbon fiber had a SEC of 0.50 meq/gm. When the tested modified fiber was transferred into the H-form again, its SEC did not change. This showed that the modifying additive did not practically wash out from the material.

To regenerate the material with cation-exchange properties it is sufficient to treat the spent material with an excess solution of sodium chloride. In order to change the modifying additive on the carbon adsorbent for another modifying additive, the strongly bound initial modifying additive of this Example (benzenesulphonate) was removed from the carbon fiber surface by treating it with the excess solution (200 ml) of 3N sodium hydroxide solution, followed by washing with water until neutrality was reached. The process of applying the modifying additive can then be repeated to obtain the desired carbon fiber adsorbent with the additional tailored ion-exchange properties.

EXAMPLE 2

The process Of Example 1 was repeated except that sodium dodecylsulphate solution (at a concentration of 1.5 gm/liter) was used as the modifying additive. The cation-exchange capacity of the activated carbon fiber material produced was increased by 0.29 meq/gm.

EXAMPLE 3

The process of Example 1 was repeated except that sodium salt of N-butylnaphthalenesulphone acid (at a concentration of 1.5 gm/liter) was used as the modifying additive. The cation-exchange capacity of the modified activated carbon fiber was increased by 0.23 meq/gm.

EXAMPLE 4

The process of Examples 1–3 was repeated, except that the adsorption column contained 1.1 gram of the activated carbon fiber. 100 ml of 0.001M disodium salt of ethylenediaminetetraacetate acid (EDTA) was passed through the column at 20 ml/min. Then the column was washed with a large quantity of distilled water until there was no longer any trace of EDTA in the washing solution. To determine the amount of strongly bound EDTA, the adsorption capacity of the modified carbon fiber toward ions of heavy metals was determined by passing 0.0009M lead nitrate solution through the column and calculating the amount of lead being adsorbed by the modified fiber. The adsorption capacity of the modified carbon fiber was found to be 0.065 mmole/gm. This result was reproduced in other experiments with a reproducibility of 10%. In contrast, the lead adsorption capacity of the initial unmodified carbon fiber was only 0.005 mmole/gm.

Modified carbon material, after adsorbing metal ions, was regenerated by passing an excess amount (200 ml) of 1M EDTA solution through the column having the spent carbon fiber. This was then followed by washing the carbon material with distilled water unit a neutral pH was reached.

In order to remove the complex forming modifying additive from the carbon material (if, for example, one wants to provide it with a different additive), the carbon fiber material was treated with steam at 150° C., followed by washing with 1M hydrochloric acid. This is then followed by a wash of 0.5M sodium carbonate and distilled water.

EXAMPLE 5

The process of Example 4 was repeated, except that hexamethyltetramine was used as the modifying additive.

The adsorption capacity of the modified adsorbent toward copper ions was 0.053 mmole/gm—ten times more than it was before the modification.

EXAMPLE 6 TO 8

10 grams of the activated carbon fiber (ACF) formed by Example 1 was placed in 1 liter of 0.01% weight/weight brilliant green solution in water (Example 6) (0.02% in Example 7 and 0.03% in Example 8, respectively). One gram of the present modified ACF adsorbed 10 milligrams of brilliant green in Example 6, 20 milligrams of brilliant green in Example 7 and 30 milligrams in Example 8. The activated carbon fiber was then washed with water and placed in a 100 cubic centimeter cylindrical column. Water containing $E.\ coli$ bacteria (2000 Index) was pumped through the column at 150 ml/min. The contact time between the modified activated carbon fiber and the $E.\ coli$ solution was 40 seconds. Filtered water was tested for the $E.\ coli$ index. The results of the analysis are: Example 6—$E.\ coli$ index of 15; Example 7—$E.\ coli$ index of 4; Example 8—$E.\ coli$ index of less than 3 (undetectable).

EXAMPLE 9

10 grams of modified ACF produced by Example 1 was immersed in 100 ml of 0.2% weight/weight brilliant green solution in ethyl alcohol. After the complete discoloration o the ethyl alcohol solution, the modified ACF was dried in the air. One gram of the modified ACF adsorbed 20 mg of the brilliant green. The activated carbon fiber was then placed in a 100 cubic centimeter cylindrical column. Water containing $E.\ coli$ bacteria (2000 Index) was pumped through the column at 150 ml/min. The contact time between the modified activated carbon fiber and the $E.\ coli$ solution was 40 seconds. The $E.\ coli$ index of the filtered water was less than 3 (undetectable).

The proposed modified activated carbon fiber material can be used for purifying tap water as well as for removing bacteria, viruses, additives and/or unwanted impurities from solutions. The impurities may be present in a wide range of concentrations, including very small concentrations common in chromatographic separations. It can also be used in medical applications (for removing unwanted blood fractions) and other applications which will suggest themselves to those skilled in the art.

What is claimed is:

1. A modified activated carbon material for removing bacteria from a liquid, comprising activated carbon fiber having an organic bactericidal compound selected from the group consisting of brilliant green, rivanol, benzyl alcohol and zephiran containing active bactericidal groups physically adsorbed thereon, said modified carbon material being capable of binding undesirable bacteria and thus removing same from said liquid.

2. The activated carbon fiber of claim 1 comprising a carbon fiber 2–10 microns in diameter.

3. The activated carbon material of claim 1 having adsorbed thereon 10–30 milligrams of brilliant green per gram of modified activated carbon fiber.

\* \* \* \* \*